United States Patent
Micu et al.

(10) Patent No.: US 8,885,464 B2
(45) Date of Patent: Nov. 11, 2014

(54) WIRELESS EEG DATA RECOVERY

(75) Inventors: Anderson Micu, Somerset, NJ (US); James G. Donnett, St. Albans (GB); Paul A. Chudy, New York, NY (US)

(73) Assignee: Bio-Signal Group Corp., Brooklyn, NY (US)

( * ) Notice: Subject to any disclaimer, the term of this patent is extended or adjusted under 35 U.S.C. 154(b) by 264 days.

(21) Appl. No.: 13/458,106

(22) Filed: Apr. 27, 2012

(65) Prior Publication Data
US 2012/0275292 A1    Nov. 1, 2012

Related U.S. Application Data

(60) Provisional application No. 61/480,155, filed on Apr. 28, 2011.

(51) Int. Cl.
*H04L 17/02* (2006.01)
*A61B 5/00* (2006.01)
*A61B 5/0476* (2006.01)
*H04L 12/26* (2006.01)
*H04L 1/18* (2006.01)

(52) U.S. Cl.
CPC ............ *A61B 5/0006* (2013.01); *H04L 43/0829* (2013.01); *H04L 1/1812* (2013.01); *A61B 5/0476* (2013.01); *Y10S 128/903* (2013.01); *Y10S 128/904* (2013.01)
USPC ........... 370/229; 370/315; 370/342; 128/903; 128/904; 341/174

(58) Field of Classification Search
CPC . H04L 69/16; H04L 43/0829; H04L 43/0864; H04L 47/10; H04L 47/283; H04L 47/16; H04L 47/12
USPC ......... 370/229, 230–232, 235, 389, 394, 412, 370/473, 477; 340/174, 870; 128/903
See application file for complete search history.

(56) References Cited

U.S. PATENT DOCUMENTS 5,963,551 A * 10/1999 Minko .......................... 370/356
6,416,471 B1 * 7/2002 Kumar et al. ................. 600/300

(Continued)

OTHER PUBLICATIONS

Bautista, Ramon Edmundo D, et al., "Incorporating Abbreviated EEGs in the Initial Workup of Patients Who Present to the Emergency Room With Mental Status Changes of Unknown Etiology", Journal of Clinical Neurophysiology, vol. 24, No. 1, (Feb. 2007), 16-21.

(Continued)

*Primary Examiner* — Dang Ton
*Assistant Examiner* — Sai Aung
(74) *Attorney, Agent, or Firm* — Schwegman Lundberg & Woessner, P.A.

(57) ABSTRACT

A system and method can have an electroencephalographic (EEG) recording module and a host device. The EEG recording can have a memory module configured to record EEG signals from a patient and a wireless transceiver configured to wirelessly transmit the EEG signals as packets. The host device can have a wireless transceiver configured to wirelessly receive at least some of the packets transmitted by the recording module wireless transceiver and a processor configured to identify one or more missing packets. Upon a completion of transmission of the packets, the host device is configured to wirelessly transmit an identity of missing packets to the recording module wireless transceiver. Upon receiving the identity of the missing packets, the recording module wireless transceiver is configured to wirelessly transmit packets including the EEG signals corresponding to the missing packets to the host device.

24 Claims, 6 Drawing Sheets

(56) References Cited

U.S. PATENT DOCUMENTS

| | | | |
|---|---|---|---|
| 6,850,769 B2* | 2/2005 | Grob et al. | 455/515 |
| 8,004,963 B2 | 8/2011 | Chang et al. | |
| 8,591,430 B2* | 11/2013 | Amurthur et al. | 600/529 |
| 2002/0109621 A1* | 8/2002 | Khair et al. | 341/174 |
| 2004/0264366 A1* | 12/2004 | Swami | 370/229 |
| 2007/0161919 A1 | 7/2007 | DiLorenzo | |
| 2007/0274342 A1* | 11/2007 | Kim et al. | 370/473 |
| 2008/0219204 A1* | 9/2008 | Lee et al. | 370/315 |
| 2009/0082829 A1* | 3/2009 | Panken et al. | 607/45 |
| 2009/0318785 A1 | 12/2009 | Ishikawa et al. | |
| 2010/0118722 A1 | 5/2010 | Lu et al. | |
| 2010/0153827 A1* | 6/2010 | Koster et al. | 714/799 |
| 2011/0251469 A1* | 10/2011 | Varadan | 600/301 |

OTHER PUBLICATIONS

Epstein, C M, et al., "American Clinical Neurophysiology Society Guideline 1: Minimum Technical Requirements for Performing Clinical Electroencephalography", Journal of Clinital Neurophysiology vol. 23, No. 2, (Apr. 2006), 86-91.

Ziai, Wendy C, et al., "Emergent EEG in the emergency department in patients with altered mental states", Clin Neurophysiol (2011), (2011), 6 pgs.

* cited by examiner

WIRELESS EEG DATA RECOVERY

CLAIM OF PRIORITY

This application claims the benefit of priority of U.S. Provisional Patent Application No. 61/480,155, entitled "MICROEEG RECORDER AND DOCKING UNIT," which was filed on Apr. 28, 2011, which is incorporated herein by reference in its entirety.

STATEMENT REGARDING FEDERALLY SPONSORED RESEARCH OR DEVELOPMENT

This invention was made with government support under award number 1RC3NS070658-01 from the National Institute of Neurological Disorders and Stroke/National Institute of Health.

The government has certain rights in this invention.

TECHNICAL FIELD

This document pertains generally to medical diagnostic devices and methods, and more particularly, but not by way of limitation, to wireless electroencephalographic (EEG) data recovery and methods for use in conjunction therewith.

BACKGROUND

Electroencephalography (EEG) refers to the recording of the electrical activity of the brain over time. Such electrical activity can be produced by the firing of neurons within the brain. EEG information can be communicated wirelessly from a detecting device. Such wireless communication can reduce wiring in medical environments, such as to enhance patient mobility or to permit the monitoring of a patient in a sterile field.

OVERVIEW

This document describes an automated wireless post-recording data integrity recovery mechanism. Streamed EEG data can be suitable for on-the-spot diagnosis of a patient condition even with relatively significant amounts of data loss. For instance, a loss of twenty-five percent or more of total data in an EEG recording session can nevertheless provide suitable information for a medical professional to diagnose a patient condition, particularly in time-sensitive environments and working with patients with acute conditions, such as an emergency room. Consequently, even in environments that cause relatively significant loss of wireless data, EEG data can still be streamed wirelessly for diagnosis of a patient condition.

However, though an EEG signal can have relatively significant amounts of data loss and still be useful, at least for an initial assessment or for diagnosing acute conditions, a long-term recording of EEG data can be desired that includes all of the recorded data for a full assessment of a patient condition or a complete record. In certain circumstances, regulatory requirements may require ultimately reliably obtaining a complete EEG record. Owing to the relatively large amounts of data in an EEG signal, it may not be practical to replace lost data while the EEG data is streaming. For instance, in some circumstances, data bandwidth can be inadequate to transmit replacement data in addition to the EEG stream. Even if available bandwidth would nominally support transmitting replacement data while streaming data, environmental conditions that can have contributed to the data loss in the first place can also inhibit immediate data recovery during streaming.

The EEG data recovery mechanism described herein provides streaming of EEG data and automatic wireless recovery of lost data after the completion of the original wireless transmission of the EEG data. An EEG monitoring session can proceed for a selected time period, during which the EEG data is streamed wirelessly as data packets from an EEG recording module to a host device. To the extent that individual data packets are not received, or are received in a corrupted condition, the data packets that are missed are noted for later recovery. Once the EEG monitoring session is complete, the identity of the missed packets is transmitted to the recording module. The recording module then transmits the missed data, such as by retransmitting the missed packets, to the host device. The host device can optionally continue to alert the recording module of missed data, and the recording module can continue to retransmit missed data, until the host device has a complete record of the EEG data.

Example 1 can include subject matter that can include a system comprising electroencephalographic (EEG) recording module, comprising a memory module configured to record a plurality of EEG signals from a patient and a recording module wireless transceiver configured to wirelessly transmit the plurality of EEG signals as a plurality of packets. The system can further comprise a host device comprising a host device wireless transceiver configured to wirelessly receive at least some of the plurality of packets transmitted by the recording module wireless transceiver and a processor configured to identify one or more missing packets, of the plurality of packets transmitted by the recording module wireless transceiver, that are at least one of (1) received as corrupted by the host device wireless transceiver or (2) missing from the at least some of the plurality of packets received by the host device wireless transceiver. Upon a completion of transmission of the plurality of packets, the host device is configured to wirelessly transmit an identity of any one or more missing packets to the recording module wireless transceiver. Upon receiving the identity of the missing packets, the recording module wireless transceiver is configured to wirelessly transmit packets including the plurality of EEG signals corresponding to the missing packets to the host device wireless transceiver.

In Example 2, the subject matter of Example 1 can optionally include that the host device is configured such that, when the missing packets correspond to an amount of data that exceeds a specified threshold, the host device suppresses transmitting the identity of the missing packets to the recording module wireless transceiver.

In Example 3, the subject matter of Example 2 can optionally include that the memory module is configured to be decoupled from the recording module and then coupled to host device, and that the host device is configured such that, when the amount of data exceeds the specified threshold, after the memory module is coupled to the host device, the host device non-wirelessly reads from the memory module the plurality of EEG signals corresponding to the missing one or more of the plurality of packets.

In Example 4, the subject matter of Example 1 can optionally include that each of the plurality of packets has a unique identifier, and that the processor is configured to identify one or more of the missing packets by an absence of the unique identifier corresponding to the one or more of the missing packets.

In Example 5, the subject matter of Example 4 can optionally include that the unique identifier of each of the plurality of packets includes an index that increments for each of the plurality of packets based on an order of transmission.

In Example 6, the subject matter of Example 4 can optionally include that the unique identifier of the one or more of the missing packets is associated with corresponding packets including the plurality of EEG signals corresponding to the missing packets, and that the processor is configured to insert the plurality of EEG signals from the missing packets into the plurality of EEG signals from the at least some of the plurality of packets received by the host device wireless transceiver according to the unique identifier of each of the plurality of packets.

In Example 7, the subject matter of Example 4 can optionally include that the host device wireless transceiver is configured to transmit ones of the plurality of packets at specified times, and that the processor is configured to identify one or more of the missing packets based on the host device wireless transceiver not having received one of the plurality of packets at the specified time.

In Example 8, the subject matter of Example 7 can optionally include that the specified times are based on specified regular intervals.

In Example 9, the subject matter of Example 8 can optionally include that the EEG recording module is configured to transmit an end recording packet upon a completion of transmission of the plurality of packets, and that the processor is configured to identify one or more of the missing packets based on the host device wireless transceiver not having received one of the plurality of packets prior to receiving the end recording packet.

In Example 10, the subject matter of Example 1 can optionally include that the host device is configured to attempt to iteratively transmit the identity of the missing packets, upon a completion of a transmission of the plurality of EEG signals corresponding to the missing one or more of the plurality of packets to the host device wireless transceiver, until the host device has received all of the plurality of EEG signals, and that the recording module wireless transceiver is configured to attempt to iteratively transmit the plurality of EEG signals corresponding to the missing one or more of the plurality of packets until the host device has received all of the plurality of EEG signals.

Example 11 can include subject matter that can include a method, comprising recording a plurality of electroencephalographic (EEG) signals from a patient in a memory module of an EEG recording module, wirelessly transmitting from the recording module wireless transceiver the plurality of EEG signals as a plurality of packets, receiving with a host device wireless transceiver of a host device at least some of the plurality of packets transmitted by the recording module wireless transceiver, identifying with a processor of the host device one or more missing packets, of the plurality of packets transmitted by the recording module wireless receiver, that are at least one of (1) received as corrupted by the host device wireless transceiver or (2) missing from the at least some of the plurality of packets received by the host device wireless transceiver, transmitting with the host device an identity of the one or more missing packets to the recording module wireless transceiver upon a completion of transmission of the plurality of packets, and transmitting with the recording module wireless transceiver the plurality of EEG signals corresponding to the missing packets to the host device wireless transceiver upon receiving the identity of the missing packets.

In Example 12, the subject matter of Example 11 can optionally include, when the missing packets correspond to an amount of data that exceeds a specified threshold, suppressing the host device from transmitting the identity of the missing packets to the recording module wireless transceiver.

In Example 13, the subject matter of Example 12 can optionally include, when the amount of data exceeds the specified threshold, decoupling the memory module from the recording module, coupling the memory module to the host device, and non-wirelessly reading the plurality of EEG signals corresponding to the missing packets from the memory module to the host device.

In Example 14, the subject matter of Example 11 can optionally include that each of the plurality of packets has a unique identifier, and identifying one or more of the missing packets is based, at least in part, on an absence of a corresponding unique identifier corresponding to the one or more of the missing packets.

In Example 15, the subject matter of Example 14 can optionally include that the unique identifier includes an index that increments for each of the plurality of packets based on an order of transmission.

In Example 16, the subject matter of Example 14 can optionally include that the unique identifier of the one or more of the missing packets is associated with corresponding packets including the plurality of EEG signals corresponding to the missing packets, and that the processor is configured to insert the plurality of EEG signals from the missing packets into the plurality of EEG signals from the at least some of the plurality of packets received by the host device wireless transceiver according to the unique identifier of each of the plurality of packets.

In Example 17, the subject matter of Example 14 can optionally include that transmitting ones of the plurality of packets occur at specified times, and that identifying one or more of the missing packets is based, at least in part, on the host device wireless transceiver not having received one of the plurality of packets at the specified time.

In Example 18, the subject matter of Example 17 can optionally include that the specified times are based on specified regular intervals.

In Example 19, the subject matter of Example 18 can optionally include transmitting with the EEG recording module an end recording packet upon a completion of transmission of the plurality of packets, and identifying with the processor one or more of the missing packets based on the host device wireless transceiver not having received one of the plurality of packets prior to receiving the end recording packet.

In Example 20, the subject matter of Example 11 can optionally include iteratively repeatedly attempting until the host device has received all of the plurality of EEG signals: receiving at least some of the plurality of packets with the host device wireless transceiver, identifying with a processor of the host device one or more missing packets, transmitting with the host device the identity of the missing packets, and transmitting with the recording module wireless transceiver the plurality of EEG signals corresponding to the missing packets.

Example 21 can include subject matter that can include an apparatus comprising a memory module configured to record a plurality of electroencephalographic (EEG) signals from a patient and a recording module wireless transceiver configured to wirelessly transmit the plurality of EEG signals as a plurality of packets. A host device wireless transceiver of a host device is configured to wirelessly receive at least some of the plurality of packets transmitted by the recording module wireless transceiver. A processor of the host device is configured to identify one or more missing packets, of the plurality of packets transmitted by the recording module wireless transceiver, that are at least one of (1) received as corrupted by the host device wireless transceiver or (2) missing from the at least some of the plurality of packets received by the host device wireless transceiver. Upon a completion of transmission of the plurality of packets, the host device is configured to wirelessly transmit an identity of any one or more missing packets to the recording module wireless transceiver. Upon receiving the identity of the missing packets, the recording module wireless transceiver is configured to wirelessly transmit packets including the plurality of EEG signals corresponding to the missing packets to the host device wireless transceiver.

In Example 22, the subject matter of Example 21 can optionally include that the memory module is configured to be decoupled from the recording module and then coupled to host device, that the host device is configured such that, when the missing packets correspond to an amount of data that exceeds a specified threshold, the host device suppresses transmitting the identity of the missing packets to the recording module wireless transceiver, and that, after the memory module is coupled to the host device, the host device non-wirelessly reads from the memory module the plurality of EEG signals corresponding to the missing one or more of the plurality of packets.

Example 23 can include subject matter that can include an apparatus comprising a host device wireless transceiver configured to wirelessly receive at least some of a plurality of packets containing a plurality of electroencephalographic (EEG) signals, the plurality of packets transmitted by a recording module wireless transceiver of an EEG recording module, and a processor configured to identify one or more missing packets, of the plurality of packets transmitted by the recording module wireless transceiver, that are at least one of (1) received as corrupted by the host device wireless transceiver or (2) missing from the at least some of the plurality of packets received by the host device wireless transceiver. Upon a completion of transmission of the plurality of packets, the host device is configured to wirelessly transmit an identity of any one or more missing packets to the recording module wireless transceiver. Upon receiving the identity of the missing packets, the recording module wireless transceiver is configured to wirelessly transmit packets including the plurality of EEG signals corresponding to the missing packets to the host device wireless transceiver.

In Example 24, the subject matter of Example 23 can optionally include that the host device is configured such that, when the missing packets correspond to an amount of data that exceeds a specified threshold, the host device suppresses transmitting the identity of the missing packets to the recording module wireless transceiver, that a memory module of the EEG recording device is configured to be decoupled from the recording module and then coupled to host device, and that, after the memory module is coupled to the host device, the host device non-wirelessly reads from the memory module the plurality of EEG signals corresponding to the missing one or more of the plurality of packets.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

System Overview

Figure 1:
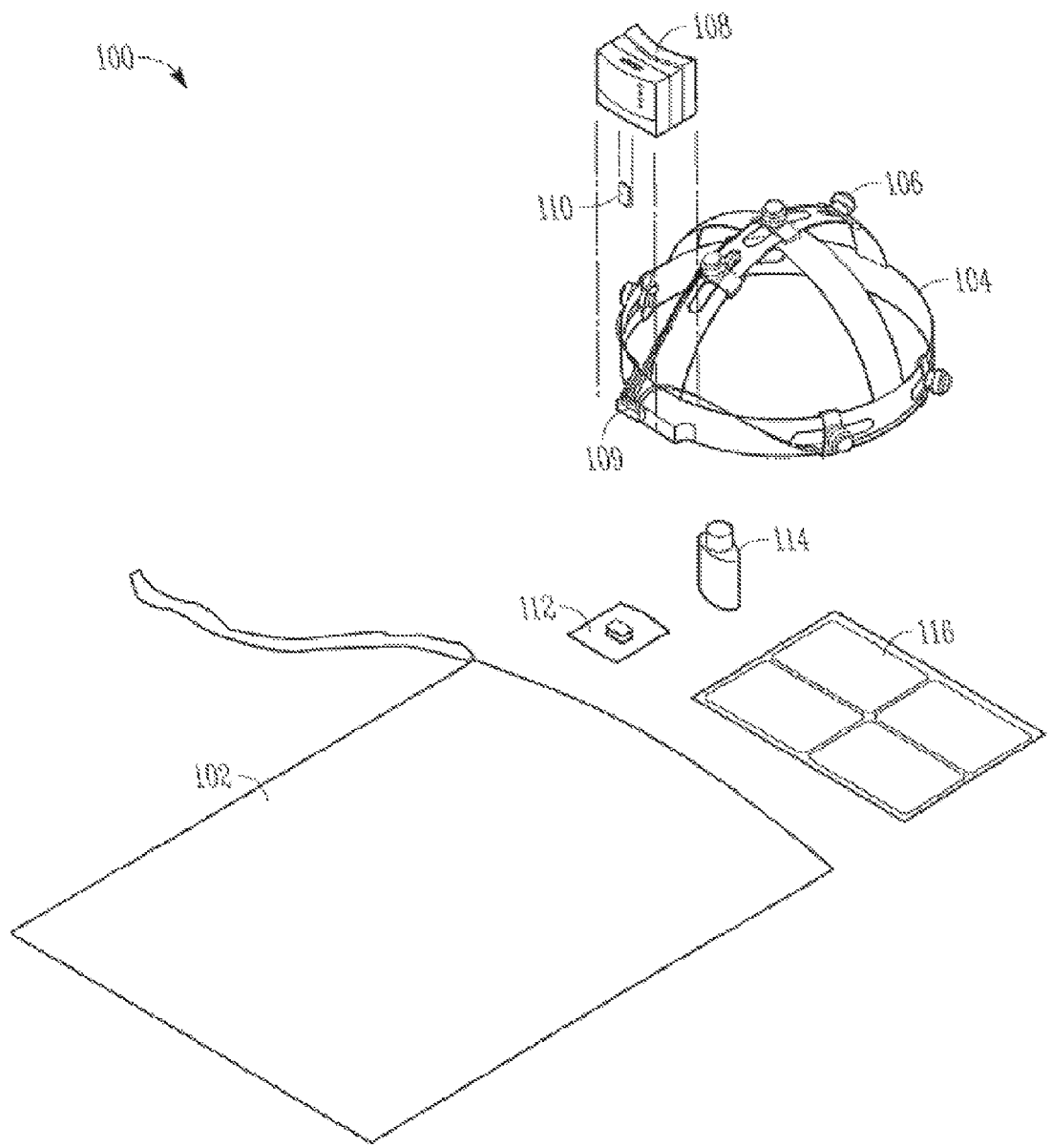
FIG. 1 shows an example of portions of the present system, including an EEG kit that can include sterilized components that can be packaged together in a kit, which can include a sterilized package such as a plastic bag.

FIG. 1 shows an example of portions of the present system, including an EEG kit 100 that can include sterilized components that can be packaged together in a kit, which can include an internally sterilized package such as a plastic bag 102. In an example, such components in the EEG kit bag 102 can include a headpiece 104, which can include multiple electrodes 106, which can be adjustably pre-mounted onto the headpiece 104. An EEG recording module 108 can be included in the kit bag 102 and can be pre-mounted onto the headpiece 104 or easily user-connectable thereto, such as via an electrical and mechanical dock connector 109 that can be located on the headpiece 104. The mechanical dock connector 109 can be located on objects nearby a patient using the headpiece 104, such as a wall, bed, chair or table. A memory module 110, as illustrated a memory card, can be included in the kit bag 102 and can be pre-inserted into the EEG recording module 108, or easily user-insertable therein. One or more spare memory modules 110 can optionally be provided in the kit bag 102, such as in a separate sealed bag. A bottle of saline solution 114 can be provided in the kit bag 102, such as to help make good conductive contact between one or more of the EEG electrodes 106 and the patient's scalp. An instruction card 116 can be provided in the kit bag 102, such as to provide instructions for use in the emergency department or another setting.

Even though the components provided in the EEG kit bag 102 can be considered disposable, the EEG recording module 108, which can include a processor circuit, memory circuit, a wireless transceiver, other electronics, and a battery, can optionally be salvaged such as for refurbishment. Such refurbishment can be by a third party service provider, who can refurbish and place the EEG recording module 108 back into the supply stream for the present system. An example of electronics, telemetry, signal processing and the like that can be included in the EEG recording module 108, such as described in James G. Donnett et al. U.S. patent application Ser. No. 11/694,816, entitled BRAIN SIGNAL TELEMETRY AND SEIZURE PREDICTION, filed on Mar. 30, 2007, which is hereby incorporated herein by reference in its entirety. Briefly, U.S. patent application Ser. No. 11/694,816 describes an ambulatory intrinsic brain signal processor circuit is coupled to a plurality of electrodes. The signal processor circuit can include a digital multiplexer circuit coupled to the electrodes to multiplex brain signal data from different electrodes together into a multiplexed data stream. An ambulatory transceiver circuit wirelessly communicates information to and from a remote transceiver. A controller circuit permits a user to control which of the electrodes contribute data, a data resolution, and whether the data includes one or both of neural action or local field potential data. Seizure prediction components and methods are also described. While U.S. patent application Ser. No. 11/694,816 emphasizes seizure prediction, its systems and methods can also be used to diagnose a seizure that is already present.

Figure 2:
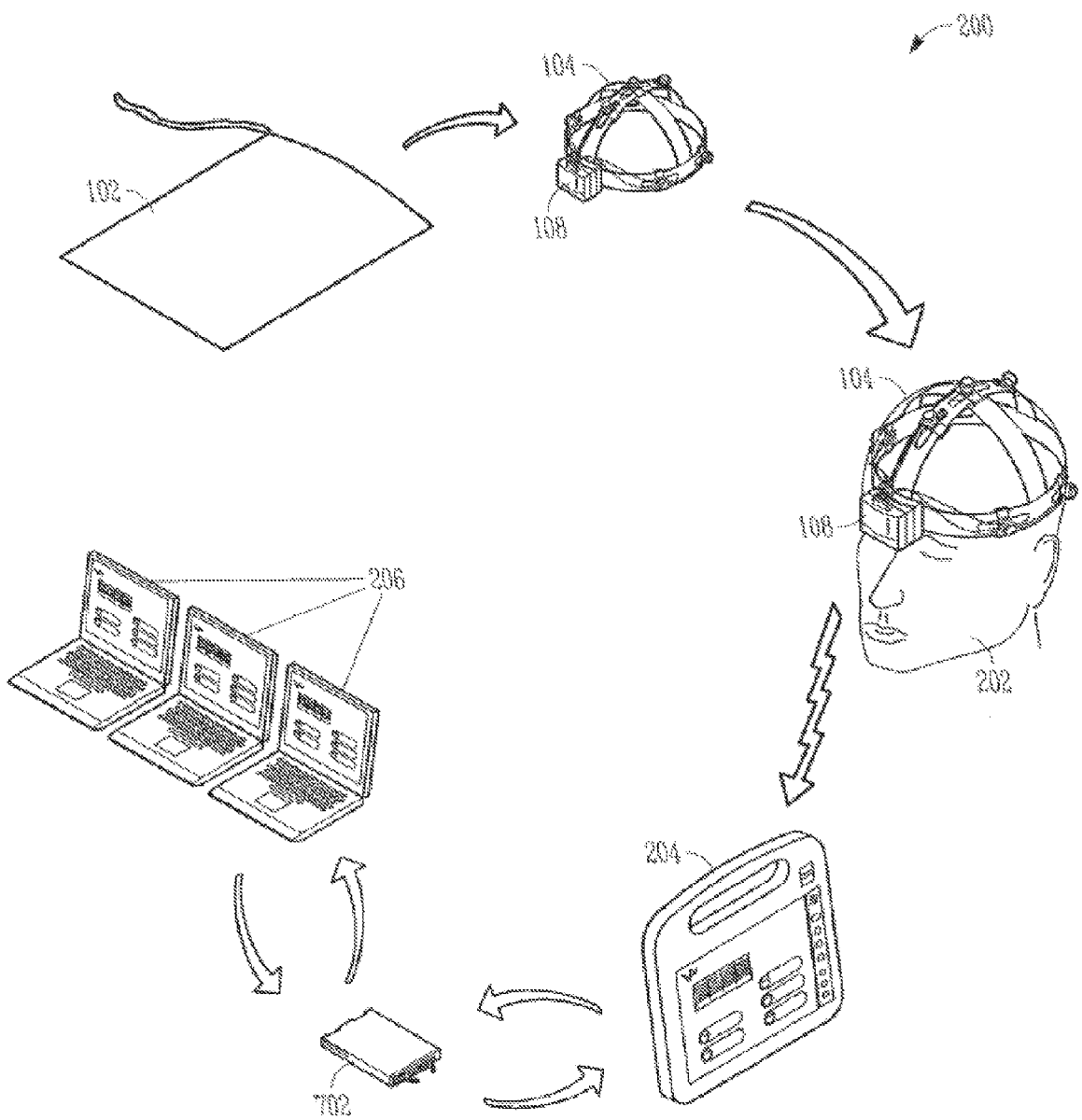
FIG. 2 shows an example of portions of the present system, in which the EEG kit bag has been opened to remove the headpiece and the EEG recording module that can be mounted thereto, such as to allow data acquisition and communication with a local or remote adjunct device.

FIG. 2 shows an example of portions of the present system 200, in which the EEG kit bag 102 has been opened to remove the headpiece 104 and the EEG recording module 108 that can be mounted thereto. The headpiece 104 can be mounted to a head of a patient 202, such as in the hospital emergency department. As will be discussed below in detail, the EEG recording module 108 can wirelessly transfer recorded EEG signals to a wireless transceiver of a host device 204, such as by using a Bluetooth or other wireless modality. As will be detailed below, the host device 204 can include a display or other user interface that can be configured to be capable of graphically displaying EEG signals. The host device 204 can include a memory circuit and a processor or other signal processing circuitry configured to process the EEG signals such as to automatically determine whether EEG signals transmitted from the EEG recording module 104 is missing or corrupted. The host device 204 can automatically determine whether a seizure or other neurological condition is present, and to display or otherwise present such resulting diagnostic information. An example of electronics, signal processing, and other circuits and techniques for determining whether a seizure condition is present or impending is described in James G. Donnett et al. U.S. patent application Ser. No. 11/694,855, entitled SEIZURE PREDICTION USING BRAIN SIGNAL TELEMETRY, filed on Mar. 30, 2007, which is hereby incorporated herein by reference in its entirety.

The host device 204 can be coupled to a wired or wireless computer or communications network, such as the internet, such as to transfer the EEG signals to one or more remote user interfaces 206. Access to the wired or wireless computer or communication network can be provided by remote data collection device 208, such as a computer or server or the like that can be located elsewhere. The remote user interface 206 can include a memory circuit, a processor circuit, or other signal processing circuitry configured to process the EEG signals such as to automatically determine whether a seizure or other neurological condition is present, and to display or otherwise present such resulting diagnostic information. An example of electronics, signal processing, and other circuits and techniques for determining whether a seizure condition is present or impending is described in James G. Donnett et al. U.S. patent application Ser. No. 11/694,855, entitled SEIZURE PREDICTION USING BRAIN SIGNAL TELEMETRY, filed on Mar. 30, 2007, which is hereby incorporated herein by reference in its entirety.

The remote user interface can optionally be used by a neurologist capable of diagnosing the EEG signals, such as to determine whether a seizure condition or other functional brain abnormality is present. The neurologist can be located within the same hospital, within the local community (e.g., at home, at a practice location, etc.) or anywhere else in the world to where such information can be communicated by the communications or computer network. The neurologist's diagnosis can, in return, be communicated back to the emergency department, where it can be used to appropriately initiate or adjust treatment of the patient.

Although FIG. 2 shows the host device 204 as not being included in the EEG kit bag 102, however, the host device 204 can be included in the EEG kit bag 102. In either case, the host device 204 can optionally include signal processing software such as for automatically diagnosing whether a seizure condition is present in the patient 202, such that remote diagnosis using the remote user interface 206 is not required, but can still optionally be used for remote verification by a neurologist of the automatic local diagnosis, if desired. The signal processing and automatic diagnosis can be performed at a remote processor, such as the remote user interface 206, or a remote computer server, if desired.

The host device 204 can include an integrated or attached video camera, such as to capture video of the patient in conjunction with the recording of the EEG. The video information can be communicated with the EEG signals to the remote user interface 206, where it can be displayed, such as to help the neurologist in diagnosing whether a seizure condition is present.

Either the local EEG recording module 108 or the host device 204 can include an interface such as to receive information from a finger cuff or other pulse oximeter, such as to acquire blood oxygen level information. The blood oxygen level information can be communicated, such as with the EEG signals, to the remote user interface 206, where it can be displayed, such as to help the neurologist in diagnosing whether a seizure condition is present.

Either the local EEG recording module 108 or the host device 204 can include an interface such as to receive information from chest electrode leads or other implantable, wearable, or other ambulatory electrocardiogram (EKG) monitor, such as to acquire heart signal information. The heart signal information can be communicated, such as with the EEG signals, to the remote user interface 206, where it can be displayed, such as to help the neurologist in diagnosing whether a seizure condition is present.

EEG Recording Module

Figure 3:
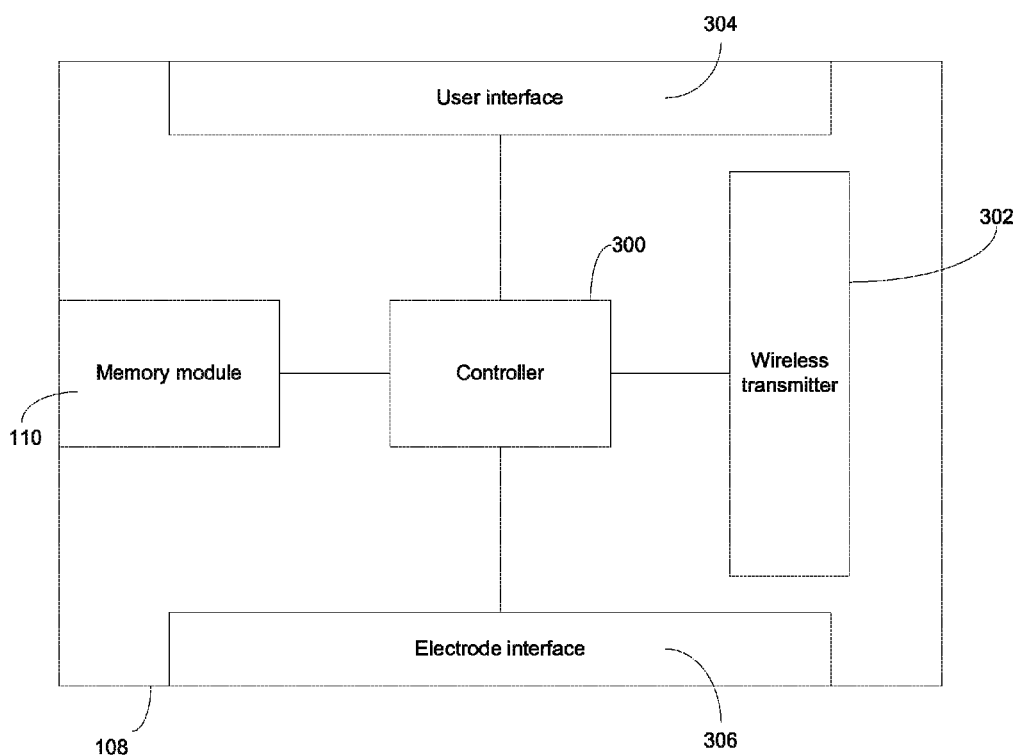
FIG. 3 shows a block diagram of an EEG recording module of the system of FIG. 2.

FIG. 3 shows a simplified block diagram of an example EEG recording module 108. The block diagram illustrates certain systems of the EEG recording module 108 and does not necessarily limit the EEG recording module 108 only to those systems. The memory module 110 can include a commercially available memory card that can be inserted into and removed from the EEG recording module 108. The memory module 110 can include memory technology that is not operationally removable from the EEG recording module 108, such as standard computer or electronic device memory like random access memory (RAM) or flash or other electrically erasable and programmable read only memory (EEPROM). The memory module 110 can include an output connector for wired transfer of data to an external device, such as the host device 204.

A controller 300 can be coupled to and can provide electronic control and response to various systems of EEG recording module 108. These systems can include the memory module 110, an EEG recording module wireless transceiver 302, a user interface 304 and an electrode interface 306. The controller 300 can incorporates electronic systems such as including a general microprocessor, internal memory and data storage, and/or device-specific controllers. The controller 300 can control the operation of any or all of the memory module 110, the wireless transceiver 302, the user interface 304, and the electrode interface 306. Some or all of the memory module 110, the wireless transceiver 302, the user interface 304, and the electrode interface 306 can incorporate native control functionality to operate either in concert with the controller 300 or independent of controller 300.

The wireless transceiver 302 can include an antenna and transmitter/receiver circuitry. The wireless transceiver 302 can optionally communicate according to one or more of various wireless data transmission modalities such as including but not limited to Bluetooth, 802.11 and cellular modalities. The host device 204 can be configured to receive the transmitted signals from the wireless transceiver 302 either directly, as may be the case with Bluetooth or Wi-Fi modalities, or indirectly via intervening transmitters and receivers, as may be the case with the cellular modality operating over a cellular network.

The user interface 304 can incorporate certain displays and inputs to allow for at least some user control of the EEG recording module 108. Buttons, switches and other inputs can permit user control, while lights and other displays can provide a user an indication of a status of the EEG recording module 108. The user interface 304 can optionally alert a user as to when EEG signals have been collected from a patient 202 and when the EEG signals have been transmitted to the host device 204. In addition, the user interface 304 can indicate to a user when the memory module 110 can be removed from the EEG recording module 108 in order to conduct a non-wireless transfer of EEG signals from the EEG recording module 108 to the host device 204.

The electrode interface 306 can provide connectivity between the EEG recording module 108 and the electrodes 106 of the headpiece 104 in order to sense EEG signals from a patient 202. The electrode interface 306 can optionally include an interface for other electrodes, such as EKG electrodes as described above. The EEG recording module 108 can record EEG signals detected by the electrodes 106 in the memory module 110. The controller 300 can process the signals, such as by digitizing the signals, to permit recording in the memory module 110. Either the controller 300 or the wireless transceiver 302 optionally can process the EEG signals into one or more packets for wireless transmittal by the wireless transceiver 302 or by a direct connection to the memory module 110.

The one or more packets for the transmittal of EEG signals from the EEG recording module 108 to the host device 204 can be configured with a portion of the EEG signals detected by the EEG recording module. The one or more packets can include all of the EEG signals detected by the EEG recording module 108 since an immediately preceding packet was created. In an example, the EEG recording module 108 creates a packet every forty (40) milliseconds and consequently includes forty (40) milliseconds of detected EEG signals.

Each packet can include a checksum value such as calculated by at least one of the controller 300 and the wireless transceiver 302. Each packet can include a unique identifier. Each unique identifier can be unique with respect to the unique identifiers of all other packets during a particular EEG signal recording session. The EEG recording module can increment the unique identifier for each subsequent packet formed to create an index.

The EEG recording module 108 can re-use unique identifiers from previous EEG signal recording sessions. Each EEG signal recording session can last for a selected period of time. The period of time can be based on an industry standard EEG signal recording session guideline. In an illustrative example, each EEG signal recording session can last twenty (20) minutes with one sample every forty (40) milliseconds and producing approximately thirty thousand packets, with each of the packets having a sequentially incremented unique identifier. Each packet can include additional information useful for inclusion in wireless data packets, such as an origination address, a destination address, and a time stamp. The time stamp can be used as a unique identifier.

The one or more packets of each EEG recording session can conclude with an "end recording" packet. Such a packet does not necessarily incorporate EEG signals, but can incorporate an indication that no more of the one or more packets incorporating EEG signals will be forthcoming for the current EEG recording session. The end recording packet can be retransmitted by wireless transceiver 302 several times to increase a likelihood of reception by the host device 204.

The EEG recording module 108 can store the EEG signals in the memory module 110 without respect to being organized into one or more packets. The EEG recording module 108 can store each packet in the memory module 110 either in addition to or instead of storage of the EEG signals themselves in the memory module 110. A user can optionally remove the memory module 110 from the EEG recording module 108, place the memory module 108 in a connector or port adapted to receive the memory module 110, and read or download the EEG signals and/or the one or more packets off of the memory module 110.

As each packet is created, the EEG recording module 108 can transmit the packet wirelessly. Doing so creates wirelessly streamed EEG data that can be received and displayed, e.g., by the host device 204. Such streaming can effectively be in "real-time", understood to include a delay in displaying the information in comparison to the event occurring that gave rise to the information that is sufficiently small as to be either imperceptible or effectively irrelevant for most uses.

Host Device

Figure 4:
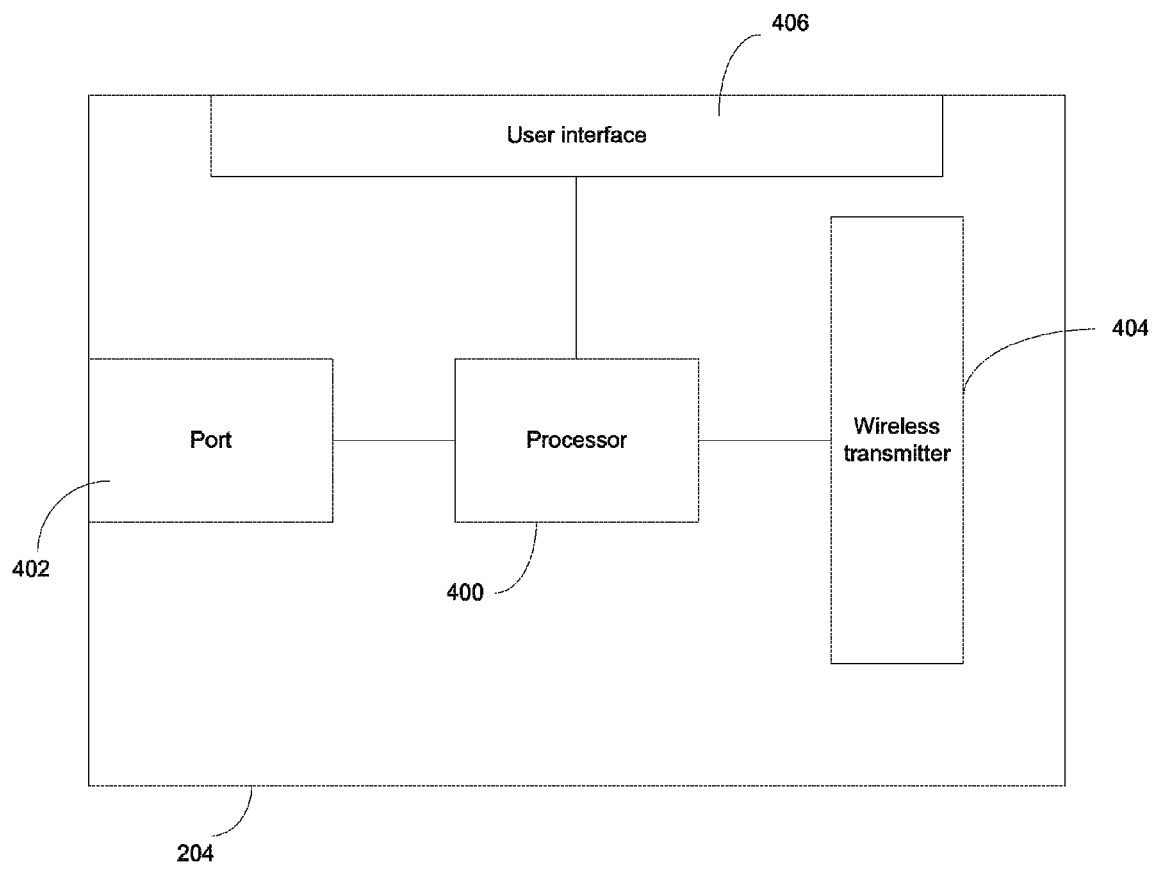
FIG. 4 shows a block diagram of a host device of the system of FIG. 2.

FIG. 4 shows a simplified block diagram of an example host device 204. The block diagram illustrates certain systems of the host device 204 and does not necessarily limit the host device 204 only to those systems. The host device 204 can be configured with stored instructions such that it can be used to do one or more of: procedure setup, input patient data, receive EEG signals, review EEG signals, and forward EEG signals to the remote user interface 206 or the remote server. A third party laptop computer, smart phone or personal digital assistant (PDA) device, net book, or medical grade tablet personal computer can be used.

A processor 400 can be coupled to and can provide electronic control and response to various systems of the host device 204. The systems of the host device 204 include a port 402 configured to couple to the memory module 110, a host device wireless transceiver 404, and a user interface 406. The processor 400 can incorporate various electronic systems such as including a general microprocessor, internal memory and data storage, and/or device-specific controllers. The processor 400 can control any or of a memory module 110 that has been inserted into port 402, the wireless transceiver 404, and the user interface 406. Some or all of the memory module 110, the wireless transceiver 404, and the user interface 406 can incorporate native control functionality to operate either in concert with the processor 400 or independent of processor 400.

The host device wireless transceiver 404 can be configured to transmit and receive electronic data according to at least one modality in common with the EEG recording module wireless transceiver 302. The common modality is Bluetooth. The wireless transceiver 404 can be configured to transmit and receive wireless data according to other modalities, including, but not limited to, 802.11 Wi-Fi and/or cellular. The wireless transceiver 404 can receive or transmit data to a transmitter and/or receiver of a third party device that is within a communication range that is consistent with a communication modality common between the wireless transceiver 404 and the third party device.

The wireless transceiver 404 can be configured in particular to receive the one or more packets transmitted by the EEG recording module wireless transceiver 302. While the host device wireless transceiver 404 can be expected to receive most of the transmitted one or more packets under most circumstances, interference in the wireless bands occupied by the common communication modality may interfere with the transmission of the one or more packets, resulting in the wireless transceiver 404 receiving only some of the packets.

The processor 400 can be configured to receive or otherwise obtain each of the one or more packets received by the wireless transceiver 404. The processor 400 can use a checksum of each received packet to determine whether the packet has been corrupted, e.g., because one or more data bits in the packet have not been received correctly or otherwise changed. The processor 400 can discard the packet if an analysis of the checksum of the packet indicates that the packet has been corrupted. Otherwise, the processor 400 can save the packet in memory.

The processor 400 can use one or more techniques, including a unique identifier of each packet and a timestamp of each packet, such as to identify one or more missing packets. The identification of one or more missing packets can occur after the processor 400 identifies corrupted packets. As such, a packet can be deemed to be "missing" if the packet was received by the wireless transceiver 404 but was corrupted, or was not received by the wireless transceiver 404 in the first instance.

If the processor 400 analyzes a first packet and determines the first packet has a unique identifier of 10,000, and then analyzes a second, immediately following packet and determines that the second packet has a unique identifier of 10,001, then the processor can conclude that a packet was not missed between the first and second packet. By contrast, if the second, immediately following packet has a unique identifier of 10,002, then the processor can conclude that a packet was missed.

The processor 400 can consider a timestamp or other chronological attribute of packets to identify missing packets. For example, one or more packets can be transmitted by the EEG recording module wireless transceiver 302 at regular intervals and at specified times. For example, packets can be transmitted at specified intervals of forty (40) milliseconds. The processor 400 can monitor a time at which packets are received by the host device wireless transceiver 404 or can compare timestamps of consecutively received packets. In the event that one or more of such chronological attributes indicate that appreciably more than forty (40) milliseconds have elapsed between consecutive packets, the processor 400 can record that one or more intervening packets were missed.

When a chronological attribute is used to identify missed packets, a unique identifier can be used by the processor 400 to create a list of one or more missed packets. The chronological attribute itself can function as a unique identifier. Thus, the processor 400 can identify packets according to a timestamp that increases by a specified time between consecutive packets. The processor 400 can use the chronological attribute and the unique identifier together to identify missed packets.

The processor 400 can use different conditions to identify a conclusion of the transmission of the one or more packets. The processor 400 can identify the conclusion of the one or more packets upon reception of the end recording packet as described herein. The processor 400 can identify the conclusion of the one or more packets based on an EEG recording session being specified as including a particular number of packets or lasting a specified time interval. Thus, when an EEG recording session is specified to include exactly thirty thousand packets, or is specified to last exactly twenty (20) minutes, the processor 400 may expect to not receive additional packets outside of those parameters. Such specified parameters and the end recording packet can aid the processor 400 in identifying one or more missed packets at the end of the one or more packets. Thus, if the processor 400 identifies a packet and then a sizable gap follows that ends either with the end recording packet or the conclusion of the specified interval of the EEG recording session, the processor 400 can conclude that all of the packets at the end of the one or more packets have been missed after the last-received packet.

Upon completion of the transmission of the one or more packets, the processor 400 can identify which packets were missed. The host device wireless transceiver 404 can then transmit to the EEG recording module wireless transceiver 302 the unique identifiers or other identifying information of the one or more missed packets. On the basis of the unique identifiers, the EEG recording module 108 can retransmit the EEG signals corresponding to the missed packets. The EEG recording module 108 can optionally retransmit the missed packets. The EEG recording module 108 can retransmit the missed EEG signals in newly formed packets.

Sometimes, the host device 204 can expect to miss relatively few packets. In general, the EEG recording module 108 and the host device 204 can include relatively reliable wireless communication modalities that do not tend to lose or otherwise corrupt packets under most circumstances. However, sometimes a source of interference or other condition internal or external to the host device 204 and the EEG recording module 108 can degrade the wireless communication link and result in relatively large numbers of missed packets. In such circumstances, it may be impractical to retransmit the missed packets wirelessly.

If more than a specified number or percentage of packets are missed, the host device 204 can optionally suppress the transmittal of the identity of the missed packets to the EEG recording module 108. In an example, if twenty-five (25) percent of packets are missed, the host device 204 can suppress the transmittal of the identity of the missed packets. At least one of the user interface 406 of the host device and the user interface 304 of the recording module 108 can optionally indicate to a user that the automatic wireless recovery of the missed packets has been suppressed. In such circumstances, the memory module 110 in the EEG recording module 108 can be removed from the EEG recording module 108 and inserted into port 402. Upon being inserted into the port 402, the processor 400 downloads the EEG signals directly and either replaces the missing EEG signals or overwrites the EEG signals from the preceding EEG recording session altogether with the EEG signals saved on the memory module 110. If the memory module 110 is not removable from the EEG recording module 108, the memory module 110 can be coupled via a wired connection to the port 402 or other input into host device 204.

The host device can include various additional or alternative functions. An integrated or attachable web camera can be provided with the host device 204, such as to allow the local user to create a video record of the patient, which can be stored as synchronized to or in correspondence with the recorded EEG signals, such as for assisting in diagnosis or documentation. In an example, a full-body video can be reduced to 3-5 frames per second (FPS), such as from a recording at thirty (30) FPS, such as to reduce the video file size.

Example of Method of Use—System

Figure 5:
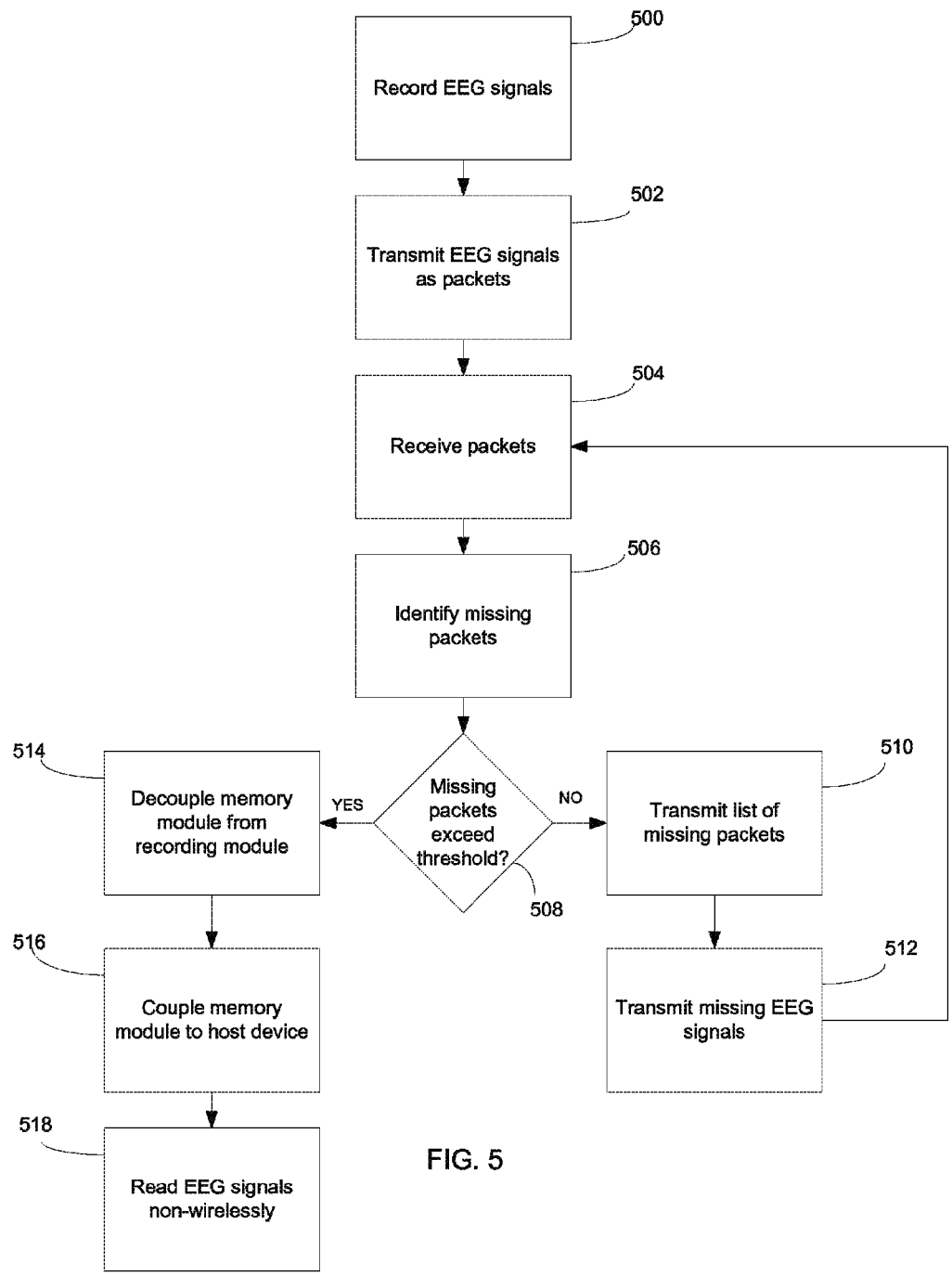
FIG. 5 illustrates an example of a method of using all or portions of the system, such as in a clinical setting.

FIG. 5 illustrates an example of a method of using all or portions of the system 200 for automated wireless post-recording EEG data recovery, such as in a clinical setting. It is emphasized that while the method will be described below with respect to the system 200 described above, the method of FIG. 5 can be applicable to any article or system that is suitably configured to implement the method steps.

At 500, the EEG recording module 108 can record EEG signals detected from the patient 202 via the electrodes 106 positioned on the headpiece 104 in the memory module 110.

At 502, the EEG recording module wireless transceiver 302 can transmit the EEG signals as one or more packets when the one or more packets are organized by the EEG recording module 108, such as by the controller 300. Step 502 can occur in parallel with step 500, transmitting the one or more packets as the one or more packets are created. The EEG recording modules wireless transceiver 302 can transmit an end recording packet upon a completion of the transmission of the one or more packets corresponding to the EEG signals.

At 504, the host device wireless transceiver 404 can receive at least some of the one or more packets transmitted by the EEG recording module wireless transceiver 302.

At 506, the processor 400 of the host device 204 can identify one or more missing packets of the one or more packets transmitted by the EEG recording module wireless transceiver 302 that are at least one of (1) received as corrupted by the host device wireless transceiver 404 or (2) missing from the at least some of the one or more packets received by the host device wireless transceiver 404.

At 508, the processor 400 can determine if the number of missing packets exceeds a specified threshold.

At 510, if the number of missing packets does not exceed the specified threshold, the host device 204 can transmit a list of the unique identifiers of the missing packets via the host device wireless transceiver 404.

At 512, the EEG recording module wireless transceiver 302 can transmit the EEG signals corresponding to the missed packets, in an example by retransmitting the missed packets. In various examples, upon the retransmission of the missed EEG signals, the system 200 then iteratively repeats 504, 506, 508, and 510 until the host device 204 has received all of the EEG signals.

At 514, if the number of missing packets does exceed the specified threshold, then a user can decouple the memory module 110 from the EEG recording module 108.

At 516, the memory module 110 can be coupled to the host device 204 at the port 402.

At 518, the plurality of EEG signals corresponding to the missed packets can be non-wirelessly read from the memory module 110 to the host device 204.

Example of Method of Use—Host Device

Figure 6:
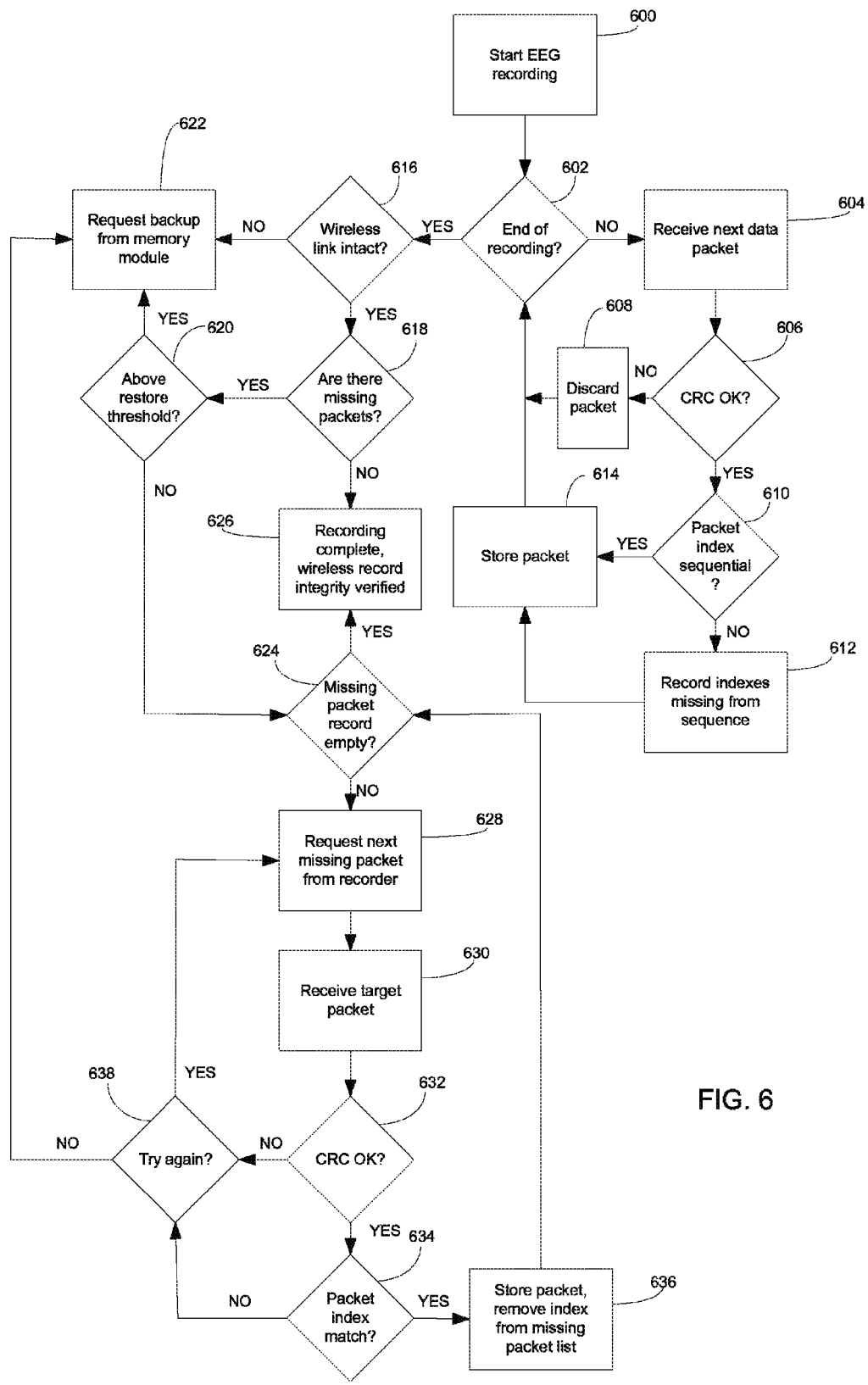
FIG. 6 illustrates an example method of operation of the host device of the system.

FIG. 6 illustrates an example of a method of using all or portions of the host device 204 such as to receive and process one or more packets transmitted from the EEG recording module 108, such as in a clinical setting. It is emphasized that while the method will be described below with respect to the host device 204 described above, the method of FIG. 6 can be applicable to any article or system that is suitably configured to implement the method steps.

At 600, the host device 204 can begin recording EEG signal data transmitted by the EEG recording module wireless transceiver 302.

At 602, the processor 400 can determine if the recording of one or more packets has ended, in an example by having received an end recording packet.

At 604, if the recording has not ended, the host device 204 can receive the next packet transmitted by the EEG recording module wireless transceiver 302.

At 606, the processor 400 can determine if the checksum of the received packet is valid.

At 608, if the checksum is not valid, the processor 400 can discard the packet and records the unique identifier, in an example an index, of the invalid packet as a missed packet.

At 610, if the checksum is valid, the processor 400 can determine if the unique identifier of the packet is in sequence with the unique identifier of the immediately received packet, in an example if the packet index is incremented over the preceding packet.

At 612, if the unique identifier is not sequential, and consequently one or more packets have been missed, the unique identifiers, e.g., the indexes, of the missing packets can be recorded by the processor 400 in a missing packet record.

At 614, the received packet can be stored in a memory of the host device 204 and the method returns to 602 to determine if the recording has ended.

At 616, the host device 204 can determine if a wireless link between the EEG recording module wireless transceiver 302 and the host device wireless transceiver 404 is intact.

At 618, if the wireless link is intact, the processor 400 can determine if there are any missing packets in the missing packet record.

At 620, if there are missing packets, the processor 400 can determine if the number of missing packets is above a specified restore threshold.

At 622, if the number of missing packets are above the specified restore threshold, the system 200 can request recovery of the corresponding missing EEG signals through directly coupling the memory module 110 to the host device 204 at the port 402, as detailed, in an example, in 514, 516, and 518 of FIG. 5.

At 624, the processor 400 can determine if the missing packet record is empty.

At 626, if the missing packet record is empty, the recording is complete and the integrity of the EEG signals as recorded in the host device 204 can be verified.

At 628, if the missing packet record is not empty, the host device 204 can request a missing packet or the corresponding EEG signals, from the missing packet record, such as by transmitting the unique identifier of the missing packet with the wireless transceiver 404.

At 630, the host device 204 can receive the missing packet or corresponding EEG signals from the EEG recording module 108 via the wireless transceiver 404.

At 632, the processor 400 can check the checksum of the received packet.

At 634, if the checksum is valid, the processor 400 can determine if the unique identifier, in an example the index, matches the requested unique identifier.

At 636, if the unique identifier matches the unique identifier of the requested packet, the host device 204 can store the packet, remove the unique identifier from the missing packet list, and return to 624 to determine if there are any more entries on the missing packet list.

At 638, if the checksum check in 632 fails or the unique identifier of the received packet does not match the unique identifier of the requested packet in 634, the host device 204 can determine whether to request that the EEG recording module 108 retransmit the requested packet by returning to 628, or whether to request coupling the memory module 110 to the port 402 in order to recover the missing EEG signals in 622. The host device 204 can optionally retransmit the packet request a selected number of times, in an example five (5)

times, before requesting non-wireless connection to the memory module 110. The host device 204 can optionally verify that the wireless link is intact as in 616 such as to determine whether to request a re-transmittal of the requested packet. Additional or alternative factors may be used to determine whether to request a re-transmittal of a packet.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description can include reference to a microprocessor, a processor circuit, a signal processor, a controller circuit, or the like. Such terms can include, among other things, a microcontroller including one or more of a volatile or non-volatile memory, multiple input/output channels, an analog-to-digital converter, a power supply, a digital-to-analog converter, or one or more other circuits, modules, or components that, in an example, can be co-integrated in a single integrated circuit, a single circuit package, a multi-chip module package, a hybrid, a polyimide flex-circuit assembly, or the like. In some examples, the implementations of such devices can be logically realized as, for example, a microcontroller, programmable logic device (e.g., field programmable gate array), state machine, or the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R, §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
an electroencephalographic (EEG) recording device, comprising:
a memory device configured to record a plurality of EEG signals from a patient; and
a recording device wireless transceiver configured to wirelessly transmit the plurality of EEG signals as a plurality of packets; and
a host device, comprising:
a host device wireless transceiver configured to wirelessly receive at least some of the plurality of packets transmitted by the recording device wireless transceiver; and
a processor configured to identify one or more missing packets, of the plurality of packets transmitted by the recording device wireless transceiver, that are at least one of (1) received as corrupted by the host device wireless transceiver or (2) missing from the at least some of the plurality of packets received by the host device wireless transceiver: wherein, upon a completion of transmission of the plurality of packets, the host device is configured to wirelessly transmit an identity of any one or more missing packets to the recording device wireless transceiver;
wherein, upon receiving the identity of the missing packets, the recording device wireless transceiver is configured to wirelessly transmit packets including the plurality of EEG signals corresponding to the missing packets to the host device wireless transceiver;
wherein the host device is configured such that, when the missing packets correspond to an amount of data that exceeds a specified threshold, the host device suppresses transmitting the identity of the missing packets to the recording device wireless transceiver:
wherein the memory device is configured to be decoupled from the recording device and then coupled to host device; and wherein the host device is configured such that, when the amount of data exceeds the specified threshold, after the memory device is coupled to the host device, the host device non-wirelessly reads from the memory device the plurality of EEG signals corresponding to the missing one or more of the plurality of packets.

2. The system of claim 1, wherein each of the plurality of packets has a unique identifier; and
wherein the processor is configured to identify one or more of the missing packets by an absence of the unique identifier corresponding to the one or more of the missing packets.

3. The system of claim 2, wherein the unique identifier of each of the plurality of packets includes an index that increments for each of the plurality of packets based on an order of transmission.

4. A system comprising:
an electroencephalographic (EEG) recording device, comprising:
a memory device configured to record a plurality of EEG signals from a patient;
and a recording device wireless transceiver configured to wirelessly transmit the plurality of EEG signals as a plurality of packets; and
a host device, comprising:
a host device wireless transceiver configured to wirelessly receive at least some of the plurality of packets transmitted by the recording device wireless transceiver; and
a processor configured to identify one or more missing packets, of the plurality of packets transmitted by the recording device wireless transceiver, that are at least one of (1) received as corrupted by the host device wireless transceiver or (2) missing from the at least some of the plurality of packets received by the host device wireless transceiver: wherein, upon a completion of transmission of the plurality of packets, the host device is configured to wirelessly transmit an identity of any one or more missing packets to the recording device wireless transceiver;
wherein, upon receiving the identity of the missing packets, the recording device wireless transceiver is configured to wirelessly transmit packets including the plurality of EEG signals corresponding to the missing packets to the host device wireless transceiver; wherein the host device is configured such that, when the missing packets correspond to an amount of data that exceeds a specified threshold, the host device suppresses transmitting the identity of the missing packets to the recording device wireless transceiver: wherein each of the plurality of packets has a unique identifier;
wherein the processor is configured to identify one or more of the missing packets by an absence of the unique identifier corresponding to the one or more of the missing packets;
wherein the unique identifier of the one or more of the missing packets is associated with corresponding packets including the plurality of EEG signals corresponding to the missing packets; and
wherein the processor is configured to insert the plurality of EEG signals from the missing packets into the plurality of EEG signals from the at least some of the plurality of packets received by the host device wireless transceiver according to the unique identifier of each of the plurality of packets.

5. The system of claim 2, wherein the host device wireless transceiver is configured to transmit ones of the plurality of packets at specified times; and
wherein the processor is configured to identify one or more of the missing packets based on the host device wireless transceiver not having received one of the plurality of packets at the specified time.

6. A system comprising:
an electroencephalographic (EEG) recording device, comprising:
a memory device configured to record a plurality of EEG signals from a patient; and
a recording device wireless transceiver configured to wirelessly transmit the plurality of EEG signals as a plurality of packets; and
a host device, comprising:
a host device wireless transceiver configured to wirelessly receive at least some of the plurality of packets transmitted by the recording device wireless transceiver; and
a processor configured to identify one or more missing packets, of the plurality of packets transmitted by the recording device wireless transceiver, that are at least one of (1) received as corrupted by the host device wireless transceiver or (2) missing from the at least some of the plurality of packets received by the host device wireless transceiver:
wherein, upon a completion of transmission of the plurality of packets, the host device is configured to wirelessly transmit an identity of any one or more missing packets to the recording device wireless transceiver;
wherein, upon receiving the identity of the missing packets, the recording device wireless transceiver is configured to wirelessly transmit packets including the plurality of EEG signals corresponding to the missing packets to the host device wireless transceiver; wherein the host device is configured such that, when the missing packets correspond to an amount of data that exceeds a specified threshold, the host device suppresses transmitting the identity of the missing packets to the recording device wireless transceiver: wherein each of the plurality of packets has a unique identifier;
wherein the processor is configured to identify one or more of the missing packets by an absence of the unique identifier corresponding to the one or more of the missing packets;
wherein the host device wireless transceiver is configured to transmit ones of the plurality of packets at specified times;
wherein the processor is configured to identify one or more of the missing packets based on the host device wireless transceiver not having received one of the plurality of packets at the specified time;
wherein the specified times are based on specified regular intervals.

7. The system of claim 6, wherein the EEG recording device is configured to transmit an end recording packet upon a completion of transmission of the plurality of packets; and
wherein the processor is configured to identify one or more of the missing packets based on the host device wireless transceiver not having received one of the plurality of packets prior to receiving the end recording packet.

8. A system comprising:
an electroencephalographic (EEG) recording device, comprising:
a memory device configured to record a plurality of EEG signals from a patient;

and a recording device wireless transceiver configured to wirelessly transmit the plurality of EEG signals as a plurality of packets; and
a host device, comprising:
a host device wireless transceiver configured to wirelessly receive at least some of the plurality of packets transmitted by the recording device wireless transceiver; and
a processor configured to identify one or more missing packets, of the plurality of packets transmitted by the recording device wireless transceiver, that are at least one of (1) received as corrupted by the host device wireless transceiver or (2) missing from the at least some of the plurality of packets received by the host device wireless transceiver:
wherein, upon a completion of transmission of the plurality of packets, the host device is configured to wirelessly transmit an identity of any one or more missing packets to the recording device wireless transceiver;
wherein, upon receiving the identity of the missing packets, the recording device wireless transceiver is configured to wirelessly transmit packets including the plurality of EEG signals corresponding to the missing packets to the host device wireless transceiver; and
wherein the host device is configured to attempt to iteratively transmit the identity of the missing packets, upon a completion of a transmission of the plurality of EEG signals corresponding to the missing one or more of the plurality of packets to the host device wireless transceiver, until the host device has received all of the plurality of EEG signals; and
wherein the recording device wireless transceiver is configured to attempt to iteratively transmit the plurality of EEG signals corresponding to the missing one or more of the plurality of packets until the host device has received all of the plurality of EEG signals.

9. A method, comprising:
recording a plurality of electroencephalographic (EEG) signals from a patient in a memory module of an EEG recording module;
wirelessly transmitting from the recording module wireless transceiver the plurality of EEG signals as a plurality of packets;
receiving with a host device wireless transceiver of a host device at least some of the plurality of packets transmitted by the recording module wireless transceiver;
identifying with a processor of the host device one or more missing packets, of the plurality of packets transmitted by the recording module wireless receiver, that are at least one of (1) received as corrupted by the host device wireless transceiver or (2) missing from the at least some of the plurality of packets received by the host device wireless transceiver;
transmitting with the host device an identity of the one or more missing packets to the recording module wireless transceiver upon a completion of transmission of the plurality of packets:
transmitting with the recording module wireless transceiver the plurality of EEG signals corresponding to the missing packets to the host device wireless transceiver upon receiving the identity of the missing packets; and
when the amount of data exceeds the specified threshold:
decoupling the memory module from the recording module; coupling the memory module to the host device; and
non-wirelessly reading the plurality of EEG signals corresponding to the missing packets from the memory module to the host device:

wherein, when the missing packets correspond to an amount of data that exceeds a specified threshold, suppressing the host device from transmitting the identity of the missing packets to the recording module wireless transceiver.

10. The method of claim 9, wherein each of the plurality of packets has a unique identifier; and
wherein identifying one or more of the missing packets is based, at least in part, on an absence of a corresponding unique identifier corresponding to the one or more of the missing packets.

11. The method of claim 10, wherein the unique identifier includes an index that increments for each of the plurality of packets based on an order of transmission.

12. A method, comprising:
recording a plurality of electroencephalographic (EEG) signals from a patient in a memory module of an EEG recording module;
wirelessly transmitting from the recording module wireless transceiver the plurality of EEG signals as a plurality of packets;
receiving with a host device wireless transceiver of a host device at least some of the plurality of packets transmitted by the recording module wireless transceiver;
identifying with a processor of the host device one or more missing packets, of the plurality of packets transmitted by the recording module wireless receiver, that are at least one of (1) received as corrupted by the host device wireless transceiver or (2) missing from the at least some of the plurality of packets received by the host device wireless transceiver;
transmitting with the host device an identity of the one or more missing packets to the recording module wireless transceiver upon a completion of transmission of the plurality of packets;
transmitting with the recording module wireless transceiver the plurality of EEG signals corresponding to the missing packets to the host device wireless transceiver upon receiving the identity of the missing packets;
wherein each of the plurality of packets has a unique identifier;
wherein the unique identifier of the one or more of the missing packets is associated with corresponding packets including the plurality of EEG signals corresponding to the missing packets; and
wherein the processor is configured to insert the plurality of EEG signals from the missing packets into the plurality of EEG signals from the at least some of the plurality of packets received by the host device wireless transceiver according to the unique identifier of each of the plurality of packets.

13. The method of claim 10, wherein transmitting ones of the plurality of packets occur at specified times; and
wherein identifying one or more of the missing packets is based, at least in part, on the host device wireless transceiver not having received one of the plurality of packets at the specified time.

14. A method, comprising:
recording a plurality of electroencephalographic (EEG) signals from a patient in a memory module of an EEG recording module;
wirelessly transmitting from the recording module wireless transceiver the plurality of EEG signals as a plurality of packets;
receiving with a host device wireless transceiver of a host device at least some of the plurality of packets transmitted by the recording module wireless transceiver;

identifying with a processor of the host device one or more missing packets, of the plurality of packets transmitted by the recording module wireless receiver, that are at least one of (1) received as corrupted by the host device wireless transceiver or (2) missing from the at least some of the plurality of packets received by the host device wireless transceiver;

transmitting with the host device an identity of the one or more missing packets to the recording module wireless transceiver upon a completion of transmission of the plurality of packets;

transmitting with the recording module wireless transceiver the plurality of EEG signals corresponding to the missing packets to the host device wireless transceiver upon receiving the identity of the missing packets;

wherein each of the plurality of packets has a unique identifier;

wherein each of the plurality of packets has a unique identifier; and wherein identifying one or more of the missing packets is based, at least in part, on an absence of a corresponding unique identifier corresponding to the one or more of the missing packets;

wherein transmitting ones of the plurality of packets occur at specified times; and wherein identifying one or more of the missing packets is based, at least in part, on the host device wireless transceiver not having received one of the plurality of packets at the specified time;

wherein the specified times are based on specified regular intervals.

15. The method of claim 14, comprising:
transmitting with the EEG recording module an end recording packet upon a completion of transmission of the plurality of packets; and
identifying with the processor one or more of the missing packets based on the host device wireless transceiver not having received one of the plurality of packets prior to receiving the end recording packet.

16. A method, comprising:
recording a plurality of electroencephalographic (EEG) signals from a patient in a memory module of an EEG recording module;
wirelessly transmitting from the recording module wireless transceiver the plurality of EEG signals as a plurality of packets;
receiving with a host device wireless transceiver of a host device at least some of the plurality of packets transmitted by the recording module wireless transceiver;
identifying with a processor of the host device one or more missing packets, of the plurality of packets transmitted by the recording module wireless receiver, that are at least one of (1) received as corrupted by the host device wireless transceiver or (2) missing from the at least some of the plurality of packets received by the host device wireless transceiver;
transmitting with the host device an identity of the one or more missing packets to the recording module wireless transceiver upon a completion of transmission of the plurality of packets; and
transmitting with the recording module wireless transceiver the plurality of EEG signals corresponding to the missing packets to the host device wireless transceiver upon receiving the identity of the missing packets; and
iteratively repeatedly attempting until the host device has received all of the plurality of EEG signals:
receiving at least some of the plurality of packets with the host device wireless transceiver;
identifying with a processor of the host device one or more missing packets;
transmitting with the host device the identity of the missing packets; and
transmitting with the recording module wireless transceiver the plurality of EEG signals corresponding to the missing packets.

17. An apparatus, comprising:
a host device wireless transceiver configured to wirelessly receive at least some of a plurality of packets containing a plurality of electroencephalographic (EEG) signals, the plurality of packets transmitted by a recording module wireless transceiver of an EEG recording module; and
a processor configured to identify one or more missing packets, of the plurality of packets transmitted by the recording module wireless transceiver, that are at least one of (1) received as corrupted by the host device wireless transceiver or (2) missing from the at least some of the plurality of packets received by the host device wireless transceiver;
wherein, upon a completion of transmission of the plurality of packets, the host device is configured to wirelessly transmit an identity of any one or more missing packets to the recording module wireless transceiver; and
wherein, upon receiving the identity of the missing packets, the recording module wireless transceiver is configured to wirelessly transmit packets including the plurality of EEG signals corresponding to the missing packets to the host device wireless transceiver;
wherein the host device is configured such that, when the missing packets correspond to an amount of data that exceeds a specified threshold, the host device suppresses transmitting the identity of the missing packets to the recording module wireless transceiver;
wherein a memory module of the EEG recording device is configured to be decoupled from the recording module and then coupled to host device; and
wherein, after the memory module is coupled to the host device, the host device non-wirelessly reads from the memory module the plurality of EEG signals corresponding to the missing one or more of the plurality of packets.

18. The apparatus of claim 17, wherein each of the plurality of packets has a unique identifier; and
wherein the processor is configured to identify one or more of the missing packets by an absence of the unique identifier corresponding to the one or more of the missing packets.

19. The apparatus of claim 18, wherein the unique identifier of each of the plurality of packets includes an index that increments for each of the plurality of packets based on an order of transmission by the recording module wireless transceiver.

20. The apparatus of claim 18, wherein the unique identifier of the one or more of the missing packets is associated with corresponding packets including the plurality of EEG signals corresponding to the missing packets; and
wherein the processor is configured to insert the plurality of EEG signals from the missing packets into the plurality of EEG signals from the at least some of the plurality of packets received by the host device wireless transceiver according to the unique identifier of each of the plurality of packets.

21. The apparatus of claim 18, wherein the host device wireless transceiver is configured to transmit ones of the plurality of packets at specified times; and
    wherein the processor is configured to identify one or more of the missing packets based on the host device wireless transceiver not having received one of the plurality of packets at the specified time.

22. The apparatus of claim 21, wherein the specified times are based on specified regular intervals.

23. The apparatus of claim 22, wherein the processor is configured to identify one or more of the missing packets based on the host device wireless transceiver not having received one of the plurality of packets prior to receiving an end recording packet.

24. The apparatus of claim 17, wherein the host device is configured to attempt to iteratively transmit the identity of the missing packets, upon a completion of a transmission of the plurality of EEG signals corresponding to the missing one or more of the plurality of packets to the host device wireless transceiver, until the host device has received all of the plurality of EEG signals.

\* \* \* \* \*